(12) United States Patent
Reiner

(10) Patent No.: US 7,933,782 B2
(45) Date of Patent: Apr. 26, 2011

(54) QUALITY ASSURANCE SCORECARD FOR DIAGNOSTIC MEDICAL AGENT ADMINISTRATION

(76) Inventor: Bruce Reiner, Berlin, MD (US)

(*) Notice: Subject to any disclaimer, the term of this patent is extended or adjusted under 35 U.S.C. 154(b) by 591 days.

(21) Appl. No.: 12/010,707

(22) Filed: Jan. 29, 2008

(65) Prior Publication Data

US 2009/0094058 A1  Apr. 9, 2009

Related U.S. Application Data

(60) Provisional application No. 60/897,837, filed on Jan. 29, 2007.

(51) Int. Cl.
*G06Q 50/00* (2006.01)
*G06Q 10/00* (2006.01)

(52) U.S. Cl. .................. 705/2; 705/3; 600/300

(58) Field of Classification Search .................. 705/2–3, 705/9; 600/300
See application file for complete search history.

(56) References Cited

U.S. PATENT DOCUMENTS

| | | | |
|---|---|---|---|
| 5,365,425 A | 11/1994 | Torma et al. | |
| 5,517,405 A | 5/1996 | McAndrew et al. | |
| 5,840,026 A | 11/1998 | Uber, III et al. | |
| 6,597,938 B2 | 7/2003 | Liu | |
| 6,970,735 B2 | 11/2005 | Uber, III et al. | |
| 2003/0036694 A1 | 2/2003 | Liu | |
| 2004/0254816 A1 | 12/2004 | Myers | |
| 2005/0156125 A1* | 7/2005 | Rimsa et al. | 250/584 |
| 2005/0234746 A1 | 10/2005 | Funahashi | |
| 2006/0030773 A1 | 2/2006 | Uber, III et al. | |
| 2006/0133995 A1* | 6/2006 | Hengerer | 424/1.49 |
| 2006/0274145 A1 | 12/2006 | Reiner | |
| 2007/0208445 A1 | 9/2007 | Gibson et al. | |
| 2007/0232885 A1* | 10/2007 | Cook et al. | 600/407 |
| 2007/0238989 A1 | 10/2007 | Hasse et al. | |
| 2008/0119717 A1* | 5/2008 | Profio et al. | 600/407 |

* cited by examiner

*Primary Examiner* — Luke Gilligan

(74) *Attorney, Agent, or Firm* — Jean C. Edwards, Esq.; Akerman Senterfitt

(57) ABSTRACT

The present invention relates to a method and apparatus where pre-defined diagnostic medical agent administration data are prospectively collected and analyzed, in order to provide an objective contrast administration risk-benefit analysis, and provide an impartial analysis for pre-testing assessment, as well as optimization of examination, contrast selection and performance parameters. By storing this data in a standardized and centralized fashion, the data could in turn be used for clinical outcome analysis on a local, regional, and national level.

46 Claims, 3 Drawing Sheets

QUALITY ASSURANCE SCORECARD FOR DIAGNOSTIC MEDICAL AGENT ADMINISTRATION

CROSS-REFERENCE TO RELATED APPLICATIONS

The present invention claims priority from U.S. provisional patent application No. 60/897,837, filed Jan. 29, 2007, the contents of which are herein incorporated by reference in its entirety.

BACKGROUND OF THE INVENTION

1. Field of the Invention

The present invention generally relates to a method and apparatus to define the multitude of data points associated with diagnostic medical agents, such as intravenous contrast, administration, and to analyze these data in a reproducible fashion to provide quality assurance feedback to various stakeholders for improved healthcare outcomes.

2. Description of the Related Art

From the time a patient seeks medical attention to the time medical treatment has been completed, a number of patient-provider interactions occur, many of which are driven by medical imaging technologies. As the sophistication and enhanced visualization capabilities of these medical imaging technologies continues to progress, new non-invasive applications are now being utilized to replace invasive procedures, theoretically improving patient safety. A pertinent example of this transition from invasive to non-invasive medical imaging would be cardiac imaging techniques used to diagnose coronary arterial disease (CAD). Up until recently, the principal diagnostic procedure of choice was coronary angiography, which necessitated direct insertion of a catheter within the coronary arteries followed by injection of a diagnostic medical agent for CAD visualization. With the advent of high-speed, multi-detector CT scanners, this invasive procedure is being replaced by non-invasive imaging techniques. While this theoretically reduces patient morbidity (associate with catheter insertion and manipulation), it does not obviate the multitude of safety issues associated with diagnostic medical agent administration, which is still required for optimized visualization of coronary arterial anatomy.

The administration of a diagnostic medical agent, such as intravenous contrast, has become ubiquitous within medical imaging and is commonly used in a number of medical imaging modalities including computed tomography (CT), magnetic resonance imaging (MRI), and digital radiography (DR). New applications and contrast agents are also being investigated for other medical imaging modalities, including nuclear medicine and ultrasound.

A number of different diagnostic medical agents are currently in everyday use, each with its own clinical profile. The overall safety analysis of diagnostic medical agent administration is largely driven by a risk-benefit analysis, which compares the clinical advantages associated with improved visualization (and corresponding improved diagnosis), with the inherent liabilities (which are largely focused on patient morbidity). In the current practice environment, this risk-benefit analysis is largely idiosyncratic in nature and in many instances is performed retrospectively, in the event of an adverse outcome (e.g., allergic reaction to intravenous contrast administration).

To date, no comprehensive medical information system is in place to collect, store, and analyze critical data associated with diagnostic medical agent administration.

Thus, a method and apparatus to provide a comprehensive medical information system associated with diagnostic medical agent administration, is needed.

SUMMARY OF THE INVENTION

The present invention relates to a computer-implemented method of administering a medical diagnostic agent, such as intravenous contrast, during an imaging examination on a patient, which includes retrieving clinical information on the patient from a database; performing an assessment of examination appropriateness for the patient by performing an analysis on the type of requested imaging examination in comparison with the clinical information retrieved on the patient; retrieving information on a plurality of diagnostic medical agents from said database; performing a functional assessment of the imaging examination to be performed by determining parameters for administration of a diagnostic medical agent during conduct of the imaging examination in light of said clinical information on the patient; and selecting and displaying an appropriate diagnostic medical agent for use during the imaging examination based on a result of said examination appropriateness assessment and said functional assessment.

In one embodiment, a QC analysis of the imaging equipment used for the imaging examination, is performed prior to the imaging examination.

In one embodiment, any iatrogenic trauma associated with insertion of an intravenous catheter for delivery of the diagnostic medical agent to the patient, is recorded. During the examination, the images acquired, QA data received, and diagnostic medical agent injection data received, is stored in the database.

After the examination, a clinical assessment of the patient is conducted after the catheter is removed.

In one embodiment, a practitioner is notified by electronic means, of any adverse reactions, unexpected or emergent findings, based on said clinical assessment.

In one embodiment, the patient is calendared for follow-up in the event of any adverse reactions or findings.

In one embodiment, an analysis of the clinical data, image data, QA data, and diagnostic medical agent administration data received during the examination, is performed, and provided in a report.

In one embodiment, any specialized image processing parameters assessed for the patient based on the functional assessment and on the imaging examination performed, is stored in the database with the QA data.

In one embodiment, institutional personnel are notified by electronic means, of any QA deficiencies in the examination or in performance of the personnel, based on the clinical data, image data, and QA data, and its analysis. If any personnel are deficient in performance or training, those personnel are denied computer access and privileges until the deficiencies are overcome.

In one embodiment, the patient is provided with a survey, and their response is added to the database for additional analysis.

In one embodiment, a trending analysis of said QA data, clinical data, image data, and its analysis, and said patient survey.

In one embodiment, best practice guidelines are stored in the database, and a comparison is performed of said QA data with said best practice guidelines, and institutional personnel are notified by electronic means, when clinical guideline thresholds are exceeded based on said comparison.

In one embodiment, economic, workflow and clinical outcomes analyses of said QA data, clinical data, imaging data, and best practice guidelines comparison, are performed.

In one embodiment, standardized QA data from the economic, workflow, and clinical outcomes analyses, as well as the analyses on the QA data, clinical data, imaging data, and the best practice guidelines comparison, are posted on the Internet for public dissemination.

In one embodiment, the information on the diagnostic medical agent is incorporated into each individual image DICOM header, and the information includes a time and/or activity curve of each organ presented which may be presented in a preselected color or size of font.

In another embodiment, a computer system for providing diagnostic medical agent administration during an imaging examination on a patient, includes at least one memory which contains at least one program which includes the steps of: retrieving clinical information on the patient from a database; performing an assessment of examination appropriateness for the patient by performing an analysis on the type of requested imaging examination in comparison with the clinical information retrieved on the patient; retrieving information on a plurality of diagnostic medical agents from said database; performing a functional assessment of the imaging examination to be performed by determining parameters for administration of an diagnostic medical agent during conduct of the imaging examination in light of said clinical information on the patient; and selecting and displaying an appropriate diagnostic medical agent for use during the imaging examination based on a result of said examination appropriateness assessment and said functional assessment; and a processor for running the program.

In another embodiment, a computer-readable medium for providing diagnostic medical agent administration during an imaging examination on a patient, includes retrieving clinical information on the patient from a database; performing an assessment of examination appropriateness for the patient by performing an analysis on the type of requested imaging examination in comparison with the clinical information retrieved on the patient; retrieving information on a plurality of diagnostic medical agents from said database; performing a functional assessment of the imaging examination to be performed by determining parameters for administration of an diagnostic medical agent during conduct of the imaging examination in light of said clinical information on the patient; and selecting and displaying an appropriate diagnostic medical agent for use during the imaging examination based on a result of said examination appropriateness assessment and said functional assessment.

Thus has, been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

DESCRIPTION OF THE INVENTION

The present invention relates to a method and apparatus where pre-defined diagnostic medical agent administration data, such as intravenous contrast administration data, are prospectively collected and analyzed, in order to provide an objective diagnostic medical agent administration risk-benefit analysis, and provide an impartial (i.e., computer-generated) analysis for pre-testing assessment. The present invention would in turn utilize this data to optimize examination and diagnostic medical agent selection and performance parameters. By storing this data in a standardized and centralized fashion, the data could in turn be used for clinical outcome analysis on a local, regional, and national level. In the end, the goal would be to optimize patient safety and improve the overall risk-benefit analysis associated with diagnostic medical agent administration within medical imaging.

Figure 1:
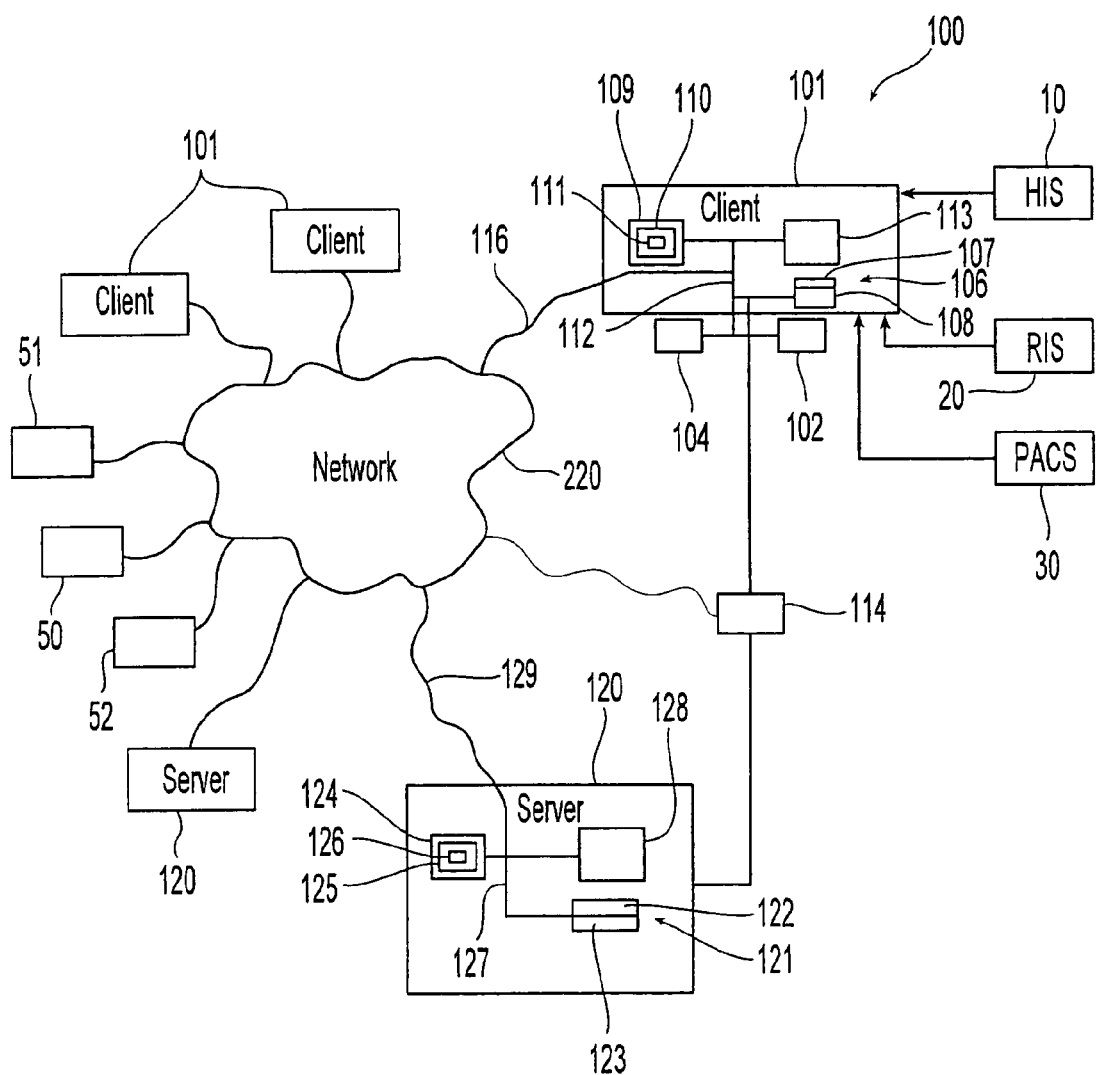
FIG. 1 is a schematic of a computer system according to one embodiment consistent with the present invention.

In the exemplary embodiment of medical (radiological) applications, the diagnostic medical agent administration system 100 of the present invention (see FIG. 1) is also designed to interface with existing systems such as a contrast injection device 5, for example, a Hospital Information System (HIS) 10, a computerized physician order entry (CPOE) system 15, a Radiology Information System (RIS) 20, a radiographic device 21 which uses, among others, a computed radiography (CR) cassette or direct radiography (DR) system, a CR/DR plate reader 22, a Picture Archiving and Communication System (PACS) 30, and to conform with the relevant standards, such as the Digital Imaging and Communications in Medicine (DICOM) standard, DICOM Structured Reporting (SR) standard, or the Radiological Society of North America's Integrating the Healthcare Enterprise (IHE) initiative.

Thus, bi-directional communication between the diagnostic medical agent administration 100 and the information systems, such as the CPOE 15, HIS 10, RIS 20, PACS 30, as well as the ancillary equipment, such as the contrast injection device 5, radiographic device 21, and CR/DR plate reader 22, allows the diagnostic medical agent administration system 100 to retrieve information from these systems and update information therein and provide the desired reports.

Although at times the diagnostic medical agent will be identified as an intravenous contrast, one of ordinary skill in the art would know that other diagnostic medical agents, such as radioisotopes used in nuclear medicine, optical imaging agents for molecular imaging, and topically administered agents for dermatology, would also be used, and the diagnostic medical agents may be administered parietally, orally, or topically.

The diagnostic medical agent administration system 100 of the present invention (see FIG. 1) includes a client computer 101, such as a PC, which may or not be interfaced or integrated with the PACS 30, and includes an imaging display device 102 capable of providing high resolution of digital images in 2-D or 3-D, for example. However, if the image resolution can be sufficiently high, the client may be a mobile terminal, such as a mobile computing device, or a mobile data organizer (PDA), operated by the user accessing the program 110 remotely from the client.

Methods and systems consistent with the present invention are carried out by providing an input means 104 (see FIG. 1), or user selection means, including hot clickable icons etc., or selection buttons, in a menu, dialog box, or a roll-down window of an interface provided at the client 101, and the user may input commands through a programmable stylus, keyboard, mouse, speech processing means, laser pointer, touch screen, or other input means 104.

The input or selection means 104 may be constituted by a dedicated piece of hardware or its functions may be executed by code instructions executed on the client processor 106, involving the display unit 102 for displaying the selection window and a stylus or keyboard for entering a selection, for example.

However, input of the symbols or icons, by a user would preferably be accomplished using a multi-functional, programmable stylus 104, which can not only be used to draw symbols onto the image, but can also accomplish other tasks intrinsic to the image display, navigation, interpretation, and reporting processes that are superior to using traditional computer keyboard or mouse methods (both within the PACS and Electronic Medical Report (EMR)).

The client 101 typically includes a processor 106 as a client data processing means, the processor including a central processing unit (CPU) 107 or parallel processor and an input/output (I/O) interface 108, a memory 109 with a program 110 having a data structure 111, all connected by a bus 112. Further, the client 101 would include an input device or means 104, a display 102, and may also include one or more secondary storage devices 113. The bus 112 may be internal to the client 101 and may include an adapter to a keyboard or input device 104 or may include external connections.

The imaging display device 102 for the present invention is a high resolution touch screen computer monitor, which would allow images, such as x-rays, to be readable clearly, easily and accurately. Alternatively, the imaging display device 102 can be other touch sensitive devices including tablet, pocket PC, and plasma screens. The touch screen would be pressure sensitive and responsive to the input of the stylus 104 which would be used to write/draw directly onto the image displaying device 102.

In addition, high resolution goggles may be used to provide end users with the ability to review images without the physical constraints of an external computer.

Note that with respect to the client system 101, the graphics user interface is a client application written to run on existing computer operating systems which may be ported to other personal computer (PC) software, personal digital assistants (PDAs), and cell phones, and any other digital device that has a screen or visual component and appropriate storage capability.

The processor 106 at the client 101 may be internal or external thereto, and executes a program 110 adapted to predetermined operations. The processor 106 has access to the memory 109 in which may be stored at least one sequence of code instructions comprising the program 110 and the data structure 111 for performing predetermined operations. The memory 109 and program 110 may be located within the client 101 or external thereto.

Note that at times the system of the present invention is described as performing a certain function. However, one of ordinary skill in the art would know that the program 110 is what is performing the function rather than the entity of the system itself.

The program 110 which runs the QA method and system of the present invention can include a separate program 110 code for performing a desired operation, or may be a plurality of modules performing sub-operations of an operation, or may be part of a single module of a larger program 110 providing the operation.

The processor 106 may be adapted to access and/or execute a plurality of programs 110 corresponding to a plurality of operations. An operation rendered by the program 110 may be, for example, supporting the user interface, data mining functions, performing e-mail applications, etc.

The data structure 111 may include a plurality of entries, each entry including at least a first storage area that stores the databases or libraries of image files, for example.

The storage device 113 stores at least one data file, such as image files, text files, data files, audio, video files, etc., in providing a particular operation. The data storage device as storage means 113, may for example, be a database, including a distributed database connected via a network, for example. The database can be a computer searchable database and may be a relational database. The storage device may be connected to the server 120 and/or the client 101, either directly or through a communication network, such as a LAN or WAN. An internal storage device 113, or an external storage device 114 is optional, and data may also be received via a network and directly processed.

In methods and system consistent with the present invention, the client 101 may be connected to other clients 101 or servers 120, including administration, billing or other systems, via a communication link 116 as a client communication means, using a communication end port specified by an address or a port, and the communication link 116 may include a mobile communication link, a switched circuit communication link, or may involve a network of data processing devices such as a LAN, WAN, the Internet, or combinations thereof. In particular, the communication link may be to e-mail systems, fax, telephone, wireless communications systems such as pagers and cell phones, wireless PDA's and other communication systems.

The communication link 116 may be an adapter unit capable to execute various communications protocols in order to establish and maintain communication with the server 120, for example. The communication link 116 may be constituted by a specialized piece of hardware or may be realized by a general CPU executing corresponding program 110 instructions. The communication link 116 may be at least partially included in the processor 106 executing corresponding program 110 instructions.

In one embodiment consistent with the present invention, if a server 120 is used in a non-distributed environment, the server 120 would include a processor 121 having a CPU 122 or parallel processor which is a server data processing means, and an I/O interface 123, but may also be constituted by a distributed CPU 122 including a plurality of individual processors 121 on one or a plurality of machines. The processor 121 of the server 120 may be a general data processing unit, but preferably a data processing unit with large resources (i.e., high processing capabilities and a large memory for storing large amounts of data).

The server 120 also includes a memory 124 with program 125 having a data structure 126 all connected by a bus 127. The bus 127 or similar connection line can also consist of external connections, if the server 120 is constituted by a distributed system. The server processor 121 may have access to a storage device 128 for storing preferably large numbers of program 110s for providing various operations to the users.

The data structure 126 may include a plurality of entries, each entry including at least a first storage area which stores image files, for example, but may also have alternative embodiments including that associated with other stored information as one of ordinary skill in the art would appreciate.

The server 120 may be a single unit or may be a distributed system of a plurality of servers 120 or data processing units, and may be shared by multiple users in direct or indirect connection to each other. The server 120 performs at least one server program for a desired operation, which is required in serving a request from the client 101.

The communication link 129 from the server 120 is preferably adapted to communicate with a plurality of clients.

The present invention is implemented in software which can be provided in a client and server environment, or in a distributed system over a computerized network across a number of client systems. Thus, in the present invention, a particular operation may be performed either at the client or the server, at the edge of a network or at the center, or both. Therefore, at either the client or the server, or both, corresponding programs for a desired operation/service are available.

In a client-server environment, at least one client and at least one server are each connected to a network 220 such as a Local Area Network (LAN), Wide Area Network (WAN), and/or the Internet, over a communication link 116, 129. Further, even though the systems contrast injection device 5, CPOE 5, HIS 10, RIS 20, radiographic device 21, CR/DR reader 22, and PACS 30 (if separate), for example, are shown as directly connected to the client 101, it is known that these systems could be connected to the client over a LAN, WAN, and/or the Internet via communication links. Interaction with users may be through secure and non-secure internet connectivity. Thus, the steps in the methods consistent with the present invention are carried out at the client or at the server, or at both, the server (if used) being accessible by the client over for example, the Internet using a browser application or the like.

The client system 101 may include communications via a wireless service connection. The server system 120 may include communications with network/security features, via a wireless server, which connects to, for example, voice recognition. However, one of ordinary skill in the art would know that other systems may be included.

In another embodiment consistent with the present invention, the client system may be a basic system, and the server may include all of the components necessary to support the software platform of the present invention. Further, the present client-server system may be arranged such that the client system can operate independently of the server system, but that the server system can be optionally connected. In the former situation, additional modules would instead be connected to the client system. In another embodiment consistent with the present invention, the client system and server system can be disposed in one system, rather being separated into two systems.

Although the above physical architecture has been described above as client-side or server-side components, one of ordinary skill in the art would know that the above components of the physical architecture may be in either client or server, or in a distributed environment.

Further, although the above-described features and processing operations may be realized by dedicated hardware, or may be realized as programs including code instructions executed on data processing units, it is further possible that parts of the above sequence of operations are carried out in hardware, whereas other of the above processing operations are carried out using software.

The underlying technology allows for replication to various other sites. Each new site can maintain "state" with its neighbors so that in the event of a catastrophic failure, other server systems can continue to keep the application running, and allow the system to load-balance the application geographically as required.

Further, although aspects of one implementation of the present invention are described as being stored in memory, one of ordinary skill in the art will appreciate that all or part of the methods and systems consistent with the present invention may be stored on or read from other computer-readable media, such as secondary storage devices, like hard disks, floppy disks, CD-ROM, a carrier wave received from a network such as the Internet, or other forms of ROM or RAM either currently known or later developed.

Further, although specific components of the system have been described, one skilled in the art will appreciate that the system suitable for use with the methods and systems consistent with the present invention, may contain additional or different components.

Accordingly, in one embodiment consistent with the present invention, the diagnostic medical agent administration system 100 and method as used in an exemplary radiology application, begins with the insertion of a catheter into a patient, through which a diagnostic medical agent (i.e., intravenous contrast) is inserted.

At the outset, the insertion of the catheter into the patient is assessed such that the party performing the insertion is properly assessed in their performance. Thus, in the present invention, a neutral third party (e.g., nurse) would first perform a patient profile assessment, which includes body habitus, clinical status, patient compliance, and venous accessibility, which takes into account inter-patient variability. This assessment by a third party of the catheter insertion would also include the recordation iatrogenic trauma associated with catheter insertion (e.g., hematoma formation, contrast extravasation, and pseudoaneurysm formation).

Performance by the technologist performing the catheter insertion would vary, depending on the ability of the technologist, and also the patient profile. For example, a technologist performing catheter insertion within a tertiary care facility dealing with high-morbidity oncology patients would not have the same success/failure rate as a counterpart working within an outside medical imaging center with a highly compliant, ambulatory patient population.

Any clinical or imaging follow-up (e.g., ultrasound) associated with this catheter-related morbidity would be documented by a third party, such as a departmental nurse, radiologist, or chief technologist, and inputted manually into the computer database, or inputted automatically by the program 110 using computerized technologies such as natural language processing software or intelligent agents. Note that the parties involved (e.g., technologist, nurse, radiologist) would be identified by the program 110 by their sign-on/login information and also by the electronic documentation (codestamping) associated with the procedure.

The program 110 will electronically link this clinical or imaging follow-up with the catheter-related morbidity, with the primary imaging examination, in the computer database 113 (or this can be done manually by the third party), thereby providing data for comprehensive outcomes and economic analyses (as discussed below). The program 110 would provide this data prospectively or retrospectively to the clinician, radiologist, technologist, or other stakeholder.

Thus, in the event that contrast extravasation is used, once the complication has been recognized by the third party or by the program 110 in a comparison of the inputted data against a standard for the procedure, departmental quality assurance policy would mandate that all relevant data be recorded, which in turn would be linked to the imaging study and patient data within the PACS 30, RIS 20, and EMR.

Accordingly, in one example, the data on contrast extravasation, including the time, volume, and pressure measurements recorded in association with contrast extravasation, as well as all subsequent orders, consultation notes, or follow-up procedures (i.e., imaging, surgical), with "contrast extravasation" incorporated into the indication and/or report, would be identified by the program 110, for example, through natural language processing (NLP) software, as related data, which would in turn be incorporated into a quality assurance (QA) database 113 by the program 110. A third party that oversees departmental quality assurance (e.g., chief technologist, administrator, or radiologist) would in turn review these quality assurance data links and determine whether it is apropos, so that all non-related data is removed from the QA database 113 associated with the patient, imaging study, and involved personnel.

In another example, when an iatrogenic hematoma or pseudoanurysm occurs with the diagnostic medical agent administration, similar data is recorded manually by the third party and tracked electronically by the program 10, with all data being recorded into the QA database 113 by the program 110. These complications are often conservatively managed, with follow-up imaging studies being performed (e.g., ultrasound or CT) to document interval resolution. In addition, all physician notes relevant to the complication (i.e., progress notes, consultation reports, operative notes) would also be linked (either manually or electronically by the program 110) and recorded within the QA database 113 by the program 110 for future analysis.

The program 110 performs a comparison analysis of the complications during diagnostic medical agent administration as compared to a standard or norm, and staff members that demonstrate poor performance indicators on a continuous basis would be expected to undergo remedial education and training sessions and be proctored until their technical scores are elevated to their peer group. Privileges are suspended are withheld by the program 110 and the administration, until remedial action is taken.

Thus, each staff member performing venipuncture and catheter insertion should have documentation of training and ongoing education, as well as performance monitoring. The training assessment of the staff member should be done on both an individual and an institutional level. This would actively encourage (and reward) continuing education for staff and provide the means with which to correlate education with technical performance.

If a staff member does not have the requisite education or training, or if their technical performance is sub-standard, then the program 110 will notify the staff member, and/or third party, and QA team, for example, that the staff member is not authorized to perform the medical procedure (i.e., intravenous contrast administration).

The standards or norms are benchmark QA criteria that are established by the department QA team (with input from technologists, administrators, radiologists, and legal), with each individual case (adverse action) also being reviewed by the QA team to ascertain the cause of the complication. In certain circumstances, where the program 110 notifies the QA team of the sub-standard performance indicators for any individual, the QA team can determine whether the adverse action was the result of human error (e.g., uncooperative patient), for example, and this is documented by the QA team into the database 113 to ensure that the individual technologist's performance record accurately reflects both the cause and severity of the adverse action.

Thus, each practitioner (technologist, nurse, and radiologist) would have their own individual data entered into the QA database 113 that records individual performance. If and when these performance indicators exceed pre-determined thresholds (established within the department and related to local, regional, and national norms), in a comparison analysis performed by the program 110, then remedial education and training is indicated by the program 110 to the QA team, for example, via various means (i.e., e-mail, fax, etc.). If the performance is deemed so poor as to compromise patient safety (as determined by the QA team or committee), privileges may be suspended or revoked and the program 110 will automatically suspend computer access until privileges are reinstated after a QA team has reviewed the records, and an approval provided.

Individual departments and imaging providers may also make some QA data available within the hospital, for example, or to the public, for the purpose of making quality metrics known, so that customers (for example, patients, clinicians, and third party payers) can make objective, data-driven decisions as to selection of imaging providers, etc. One of the mandates of pay-for-performance (P4P) programs is to make quality related data available to the public for informed decision-making and this can be done by partially tying provider payments to the sharing of this data.

Also, by use of this QA system, administrators can appropriately delegate clinical and technical responsibilities to staff members who exhibit the highest performance.

Another feature of the present invention is the assessment of exam appropriateness which may be performed by the program 110. This assessment provides an objective means to ascertain whether the appropriate exam parameters are being utilized, based on the clinical indications and patient history provided. Computerized physician order entry (CPOE) systems 15 may provide the technical means to accomplish this task with ordering clinicians required to input the pertinent clinical indication and patient history into the database 113, as well as for assessing exam appropriateness based on the clinical data provided (using artificial intelligence in the form of neural networks).

In addition to the assessment of exam appropriateness, the program 110 performs a functional assessment of how the pre-selected imaging exam is to be performed. For example, an abdominal CT exam may be performed in an unlimited number of ways, based on the presence or absence of a diagnostic medical agent, the manner in which the diagnostic medical agent is delivered, the various phases of image acquisition (relative to diagnostic medical agent delivery), as well as the various processing parameters employed. The selection of these "contrast related" parameters by the program 110 must take into account a multitude of clinical, historical, and laboratory data unique to each individual patient. Using the same abdominal CT analogy, five different patients could be referred to an imaging department by the radiologist after assessment/notification by the program 110, for assessment of abdominal pain and suspected abdominal aortic aneurysm. Based on the individual patient-specific data outlined below in Table 1, the appropriate selection of the imaging exam, technique, and diagnostic medical agent administration by the program 110 and the radiologist, would vary.

TABLE 1

|  | Body Habitus | Patient Compliance | Renal Function | Allergic History | Recommended Exam |
|---|---|---|---|---|---|
| Patient A | Thin | High | Good | No allergies | CT+ |
| Patient B | Thin | Medium | Good | Iodine allergy | CT− or US |
| Patient C | Thin | Poor | Poor | Unknown | US |
| Patient D | Obese | High | Good | No allergies | CT+ |
| Patient E | Obese | Medium | Good | Iodine allergy | CT− |
| Patient F | Obese | Poor | Poor | Unknown | CT− |

Specifically, in the case of the above patients, the program 110 would compare Patients A, B, and C, and note differences in compliance, renal function, and allergic history. As a result of poor renal function and an uncertain allergy history; the program 110 would determine that the preferable imaging study for Patient C would be an ultrasound (in lieu of CT). Patient F has the same profile as Patient C, with the exception of a different body habitus, which would limit patient F's ability to replace CT with ultrasound (because ultrasound is largely dependent upon patient size, whereas CT is not).

The program 110 would determine that Patients A and B would both be CT candidates, except that the history of iodine allergy may effect the decision as to whether or not intravenous contrast, for example, should be administered, and if so, what type of contrast would be appropriate. If for example, Patient B's electronic medical record (EMR) has documentation of a recently performed contrast-enhanced CT exam without adverse reaction, then the program 110 would determine this fact and recommend contrast administration (using the same contrast agent) as appropriate. If on the other hand, Patient B's EMR notes a prior allergic reaction (e.g., urticaria) from a prior contrast-enhanced CT, then the program 110 would recommend the preferred exam as an ultrasound or non-contrast CT. For Patient E, (who has the same profile as patient B, except differences in body habitus), the program 110 would determine the preferred imaging exam as non-contrast CT, due to technical limitations associated with ultrasound in an obese body habitus. For Patients A and D, the preferred imaging exam would be determined by the program 110 to be contrast-enhanced CT, although the volume of contrast administered and processing parameters utilized may vary depending on differences in patient weight.

In addition to the assessment of exam appropriateness and patient safety, clinical assessment of the exam performed is another variable contained within the Contrast QA Scorecard of the present invention. In addition to the program 110 determining the appropriateness of contrast administration, radiologists and clinicians are tasked with ensuring the maximal diagnostic information is contained within the imaging exam performed, thereby improving diagnostic accuracy and medical/surgical treatment.

In one example, a patient with newly diagnosed colon cancer presents for a staging CT of the abdomen and pelvis. Based on the patient profile and clinical indication, it is determined by the program 110, and affirmed by the clinician and radiologist, that the appropriate exam is a contrast-enhanced CT. In the course of defining the protocol for this exam, the radiologist directs the technologist as to the type, volume, and rate of contrast administration. In one scenario, the radiologist may instruct the technologist to obtain images during both the arterial and venous phases of liver enhancement, while in a second scenario the radiologist simply defers to the technologist, who acquires images in the venous phase of enhancement only.

While both exams utilize the same volume and type of diagnostic medical agent, one exam (with biphasic imaging), acquires additional data that ultimately leads to improved diagnosis (in both accuracy and confidence of diagnosis). As a result of the more definitive report associated with the biphasic exam, the clinician would in all likelihood provide a higher clinical assessment score for this exam, as opposed to the "standard" single, phase CT exam. This clinical assessment is recorded in the database 113 by the program 110 as part of the Contrast QA Scorecard for further analysis on an individual, department, and institutional basis. In addition, follow-up imaging studies, clinical tests, and pathology reports would be recorded by the program 110 to further differentiate radiologist performance in overall economics and outcomes analysis.

Thus, once the program 110 makes an assessment of exam appropriateness, the responsible clinician and radiologist, who collectively are responsible for assessing the patient's clinical status and history, would confirm the optimal imaging exam.

Once the exam type is determined by the program 110 and affirmed by the clinician and radiologist, the manner in which contrast is administered is the primary responsibility of the radiologist, who is tasked (based on clinical training and expertise), with ensuring contrast is administered in the appropriate fashion to maximize patient safety and clinical efficacy.

Clinical adverse outcomes resulting from contrast administration (e.g., nephrotoxicity, pulmonary edema, anaphylaxis) are electronically recorded by the program 110 in the patient's medical record (e.g., EMR) and duplicated within multiple information systems (PACS 30, RIS 20) for redundancy, as well in the centralized QA database 113. In addition, these adverse outcomes are recorded by the program 110 in the radiologist and clinician's QA databases 113 for documentation, analysis, and educational purposes.

In addition to the aforementioned clinical data contained within the Contrast QA Scorecard and which is provided to predetermined users (i.e., QA team, etc.) by the program 110, technical data is an important component and is largely tied to injector technologies. The technical data is acquired directly from the contrast injection device 5 by the program 110 and stored in the database 113. The contrast injection device 5 stamps the data from the contrast injection device 5, and records the type and volume of contrast administered, injection rate and pressures, and contrast extravastion. These data can be stored in the database 113 by the program 110 and directly correlated with the imaging modality (e.g., CT, MRI) to provide a direct linkage between contrast delivery and the derived imaging data. This provides information on both patient safety as well as the specific imaging protocol employed.

In another embodiment, the program 110 incorporates diagnostic medical agent information, such as contrast-related data, into each individual image DICOM header. In this embodiment, the radiologist would place a cursor on the monitor 102 over any region on the displayed image and the program 110 would provide contrast-data specific to that volumetric data point, which can be used for diagnosis, quality assessment, or physiologic assessment.

If, for example, the user wanted to determine differential perfusion to the kidneys, the user could place the cursor over each individual kidney and review the time-activity curve of each kidney presented on the display 102 by the program 110, to compare and contrast differential renal perfusion. This could be done by the program 110 for a single kidney, or comparing two kidneys, or even the one kidney over time (relating contrast data from two different studies). Since the data is recorded and tracked in a standardized fashion by the program 110, it is directly comparable, regardless of the equipment (CT) manufacturer, technologist performing the exam, or changes in technique.

The same principle could be applied to an area of pathology (e.g., renal tumor), which provides a standardized mechanism to assess tumor perfusion. This could be important for treatment planning, assessing response to therapy, or guiding surgical intervention.

In one example, a CT protocol for CT of the kidneys includes information for both the scanning protocol such as mAS and kVP and slice thickness and other parameters as well as the contrast injection protocol. The program 110 would provide a functional assessment, where the patient is recommended for a scout image of the abdomen that does not involve injection of contrast. Thus, the injector 5 does not inject contrast and the program 110 would generate a DICOM image that has a field that indicates that the image was unenhanced.

The patient then has an unenhanced CT of the kidneys and the program 110 would not allow the injector 5 to inject contrast and those images are all labeled by the program 110 as unenhanced.

At a later date, the patient then has a contrast enhanced series obtained with triggering off the abdominal aorta. A region of interest is automatically drawn by the program 110 over the suprarenal abdominal aorta (or this can be manual), and images at super low dose are obtained at that level by the program 110, and the program 110 directs the CT scanner 21 for the injector 5 begin the injection of contrast. A trigger of 150 Hounsfield units is used to begin the scan of the abdomen at regular dose.

The injection protocol calls for an initial bolus of 2 cc's per second with a linear rise over 5 seconds to 4 cc's per second which is then maintained for a total of 20 seconds during administration. Subsequently, the program 110 has the injector 5 inject the contrast at a rate of 2 cc's per second for the next 20 seconds.

The program 110 has the injector 5 send information about the contrast injection protocol including time/activity curve (precise injection rate at each time period and when the injection started and stopped) to the database 113. This would include pressure information and whether or not there was evidence of soft tissue extravasation. It would also include amount of contrast used the type of contrast used and any problems with the injector.

After a few minutes, a delayed set of images is obtained by the program 110 without injection of additional contrast material. Since these images were obtained after a contrast injection occurred, they are labeled by the program 110 accordingly (e.g., the first image would indicate that it was obtained 5 minutes and 50 seconds after the start of the contrast injection profile recorded on the previous series including the bolus tracking information). Thus, these images would not be labeled as unenhanced by the program 110 but with their own unique contrast profile that would indicate how long the delay was after the injection of contrast.

When viewed, the program 110 would allow the radiologist or technologist or clinician, or other reviewer, to see on the display 102 where any individual slice fell on a time contrast injection activity curve. The information could be displayed in a number of ways including the curve itself, or using a color or size of font scheme to indicate where the image fell in the contrast injection timing including amount and pressure and whether extravasation occurred. This would allow the user to determine whether the contrast injection timing was adequate for the imaging and allow subsequent adjustment and fine tuning of the contrast injection on subsequent studies performed on the patient. It would also permit cumulative contrast amount tracking by the program 110, and the program 110 could also track the patient's GFR, creatinine, BUN or other pertinent laboratory studies in the DICOM information as well or as a separate file.

Thus, in one example, this more specialized protocol sequentially obtains CT images during different phases of contrast administration (arterial, venous, and excretory phases). The data recorded by the program 110 would not only identify the volume and type of contrast, but also the injection rates and specific times and sequences of image acquisitions. This may be important in certain types of diagnoses and overall interpretation accuracy.

This recorded information can also be used prospectively by the program 110 to determine the optimal imaging/contrast protocol in accordance with the clinical indication. If, for example, the patient has a suspected renal malignancy, then the program 110 would be able to provide an "optimal" imaging protocol that is disease-specific (based on the scientific literature and established clinical guidelines).

After contrast is administered, an image study is taken of the patent by a technologist based on the clinician's instructions, using the radiographic device 21, and the cassette is read at plate reader 22. The various QA data points taken during the diagnostic medical agent administration and following exam, are recorded in the QA database 113 by the program 110 using extensible mark-up language (XML) schema. Individual XML tags are applied to each individual QA data point, which would initially reside in the primary technology in which it was acquired or recorded (e.g., RIS 20, PACS 30, EMR, injector 5, and modality).

In performing the exam, the number of quantitative metrics (QA data points) contained within the Contrast Scorecard could be proactively accessed, referenced, and analyzed to provide the performing technologist with recommendations to optimize exam quality and patient safety. The data analyzed within the Contrast Scorecard for the purposes of technologist decision support would include (but not be limited to) the following: Patient Profile (body habitus, age, clinical indication, past and current medical/surgical history); Contrast Safety Profile (organ toxicity, allergic reactions, side effects); Contrast Efficiency (Time activity curve analysis); Volume of Contrast; Timing of Contrast Administration; Site of Intravenous Access; Modality (Used for Data Acquisition); and Acquisition Protocol.

In the case of a portable ICU chest radiograph for example, the technical acquisition data would be presented to the technologist at the time of a later comparable exam being performed. In addition to the acquisition parameters used from prior comparable exams, the corresponding image quality metrics contained within the QA database 113 (both subjective and objective) would be cross-referenced by the program 110 to identify the optimum exposure parameters to use for the current study. This could take into account multiple variables unique to the current exam including change in patient clinical status, indication for the current exam, and changes in technology used. By cross-referencing the patient and institutional specific QA databases 113 with those of regional, national, or international databases; the program 110 would present the technologist with a compendium of analytical data which would offer the optimum exposure parameters for the exam to be performed. Much of this cross-referencing of QA data would be performed automatically by the program 110 at the time of computerized order entry.

Thus, when preparing for the examination to be performed, the technologist would review the data automatically transferred by the program 110 from the injection device 5, CPOE 15, PACS 30, RIS 20, and EMR and input key variables into the QA and Contrast Scorecard databases for prospective analysis and recommendations for contrast optimization parameters. Based on the program's 110 recommendations and/or data, and the additional input from key stakeholders (e.g., referring clinician, interpreting radiologist, departmental administration), the technologist may input a hierarchical list of variables, which in turn prompts the program 110 to present the technologist with a list of "preferred" options for exam protocol, contrast agent, volume/timing of contrast administration, and image processing algorithms for enhanced diagnosis.

In one detailed example, a patient may have had a recent myocardial infarction (MI) or inflammation of the heart muscle (myocarditis), either one of which could result in a substantial decrease in cardiac function. Because patient condition can change quite dramatically over a short period of time, the methodology used for image acquisition and contrast administration must also change in accordance to the patient profile, in order to simultaneously maximize patient safety and exam efficacy. As a result of this significant change in clinical status of the patient, the optimized contrast parameters would need to be changed based on changes in the patient profile, such as newly diagnosed CHF, weight loss/gain, and recent surgery (nephrectomy).

The program 110 would search the Contrast and QA databases 113 for prior comparable imaging studies (CTA heart) in this patient, and return the result that optimized image quality may be determined to occur with an injected contrast volume of 100 cc at a rate of 2 cc per second. However, with the change in cardiac function this would no longer be applicable, since repeating these contrast administration parameters in the patient's current clinical status would likely result in a complication such as pulmonary edema. Recognizing this change in the patient profile, the program 110 would notify the technologist of this problem. Then, the technologist could proceed in a number of ways to modify the contrast protocol with the assistance of decision support tools integrated into the Contrast Scorecard program 110.

For example, the technologist may consult the database 113 to find recommendations for contrast administration at different levels of cardiac function. By entering in the exam to be performed (CTA Heart), the patient's most reject cardiac ejection fraction (24% by echocardiography), patient renal function (creatinine) and the patient weight, the program 10 will provide a generic recommendation for contrast volume and injection rate for a number of different contrast agents.

The technologist may then query the institutional Contrast/QA databases 113 for prior patient and exam-specific contrast data. When the program 110 identifies the optimized contrast-related protocol, the technologist inputs the "critical patient change" to the program 113 and either selects the variable from a pre-determined pick list presented by the program 10, or manually enters the critical change (decreased cardiac function). The program 10 then cross-references this changing variable within its database 113 and makes recommended modifications to the contrast administration parameters based on its intrinsic knowledge base 113 and data analyses (of similar patient profiles and exam types).

In another embodiment, the technologist may also repeat the same steps as previously, but in this case, may elect to query a multi-institutional database 113 (regional, national, international) that can incorporate a number of additional optional data points into the analysis including (but not limited to) the specific contrast agent to be used, the specific acquisition technology employed, the exact site of intravenous access, and the method of contrast injection (e.g., specific type of automated injector). By searching larger databases 113, the program 110 can generate a greater number of recommendations for contrast administration, which take into account these additional variables.

Thus, in the above examples (CHF, weight gain/loss, or recent surgery), the technologist would input the "changing patient profile" variable and the program 110 would prompt the technologist with relevant questions. In addition, the Contrast Decision Support portion of the program 110 could automatically query relevant information technology (IT) databases 113, such as the patient electronic medical record (EMR) for additional data. In the case of recent surgery (nephrectomy), the removal of one kidney would likely result in change of the patient's overall renal function, which can be measured by several laboratory measures (e.g., creatinine, glomerular filtration rate (GFR)). If neither the technologist nor EMR has this relevant data available for correlation at the time of exam performance, the program 110 may recommend a number of options to the technologist, such as: 1) perform the requisite exam without contrast administration; 2) change the exam selection to an alternate imaging exam, which does not require diagnostic medical agent; or 3) obtain pertinent laboratory data prior to performing the exam as ordered.

The program 110 would also search the patient EMR for related medical data, such as other medical conditions that could impair renal function (e.g., diabetes), that might have an additive impact on renal deterioration. With this additional knowledge in hand, the program 110 may alert the referring clinician or interpreting radiologist (via an e-mail or text message) of the clinical concerns and request further clarification of exam status. This multi-directional communication would be electronically recorded in the Contrast and QA databases 113 with receipt confirmation. The "high alert" status generated would automatically be recorded by the program 110 into a special QA folder for additional clinical/peer review (i.e., QA team). Each technologist, referring clinician, and interpreting radiologist would also have these data entered into their own individual QA/Contrast Scorecards for patient safety analyses.

In the event an adverse outcome resulted from contrast administration (e.g., renal failure), the program 110 would automatically flag the case in the Contrast and QA Scorecard institutional databases 113, for additional peer review and outcome analysis. This data would also be transmitted by the program 110 to corresponding regional and national "adverse outcomes" databases 113, which could be used for individual credentialing, institutional accreditation, provider education, pay for performance measures, and research/product development.

Thus, once the diagnostic medical agent is administered, the radiographic exam is taken according to known techniques. Once the exam has been completed (as designated by clinician receipt of the final report), the images taken are automatically forwarded to the PACS 30 by the program 10, and then to the computer imaging display device 102 for display and then to the QA database 113 for storage. The images are then analyzed and utilized by the program 10 for comprehensive reporting.

Optimization of diagnostic medical agent is determined by the program 110 by including the modality (e.g., CT or MRI), power injector 5 (for contrast administration), and PACS 30 (for image archival and review). In addition to these three core technologies, a number of ancillary technologies have the potential to also become integrated into contrast optimization, specifically as it relates to the interpretation process. These consist of decision support technologies which include (but are not limited to) computer aided detection/diagnosis (CAD), segmentation analysis, textual analysis, and automated data mining.

The following are critical components in the standardization of contrast-related data, and the program 110 records these components as a number of data points which are contained within the Digital Imaging and Communications in Medicine (DICOM) header. The components are: Time—Starting time of contrast administration (can be single or multiple), Ending time of contrast injection (can be single or multiple), Specific time of each individual image relative to contrast start time; Contrast Agent—Specific type of contrast agent, Osmolality of contrast agent, Total volume administered, Delivery Methodology; Method of contrast administration—Rate of contrast injection (can be single or multiple: Volume of contrast administered (at time of each individual image acquisition), Anatomic site of access for contrast delivery; Catheter size, Attenuation Values—Attenuation value of specific anatomic region of interest (ROI) (specific to each individual image), Differential attenuation values (of these ROIs over time), Change in attenuation relative to pre-contrast ROI; Complications—Iatrogenic complications (extravasation), Allergic reactions (type and severity), Treatment of complications, Patient disposition; Technology—Image acquisition, Image processing, Contrast delivery, Data storage.

The above standardized data can be incorporated into the DICOM header for each medical image, which provides a standard mechanism for data storage within medical imaging and information technologies.

Thus, using the Contrast Scorecard and standardization of contrast-related data, the injector 5, modality, and PACS 30 would communicate and share data with one another, thereby creating a universal contrast database 113. In addition, the program 110 would use the standardized data to create a mechanism by which an individual practitioner (e.g., radiologist, clinician, and technologist) could review any image contained within the comprehensive imaging dataset and identify critical information related to anatomy, pathology, and contrast indicators. By the program 110 storing the data within each individual image's DICOM header, the image could be reviewed in a standard format (independent of the imaging modality and PACS used), and standardized data could be extracted related to contrast administration by the program 110.

The above technical data tied to contrast administration can be supplemented by equipment quality control (QC) data, which measures equipment performance and calibration, at the levels of the imaging modality and injector technologies. The QC can be performed by technologists or medical physicists, using phantoms. In addition, some technologies use automated QC programs provided by specialized computer software programs. The data is stored in the database 113 by the program 110 and provided with the contrast information data for comprehensive review by the QA team etc.

Further, by creating standardized data related to contrast administration, the program 10 can tailor (i.e., customize) the decision support technology to the contrast-enhanced imaging data. For example, the current CAD technologies take a "one size fits all" approach, where a single CAD algorithm is applied to the imaging dataset, regardless of the variability in contrast enhancement. If, as an example, a CAD program is applied to a CTA of the thorax (in the detection of pulmonary emboli), the CAD program is not designed to modify to differences in pulmonary arterial enhancement, which is currently highly variable. However, in the present invention, the program 110 can include a contrast-specific CAD program, which utilizes slightly different algorithms, depending upon the degree of pulmonary arterial contrast enhancement. By creating standardized contrast-data tied to each individual image, the CAD algorithm could be modulated (literally on an individual image basis) by the program 110, in accordance with the degree of contrast enhancement. Through the creation of large contrast datasets (using the aforementioned standardized contrast imaging data), both researchers and vendors could have access to meta-data to optimize decision support technologies (specific to differential contrast enhancement), as well as creating best practice guidelines and standards relating to contrast imaging data.

Patient subjective feedback provides additional data in assessing individual and institutional customer service. Patient satisfaction surveys can be electronically sent and/or administered to patients by the program 110 following completion of their imaging exams, to assess a number of subjective data including, for example, professionalism of staff, technical proficiency (in obtaining intravenous access), informed consent (explanation of procedure and satisfactory response to questions), overall comfort during exam performance, symptoms (and adverse actions) related to contrast administration, and timeliness of examination.

Additional QA variables for handling by the institution/administrator would include patient education (including informed consent), remedial staff education and training, and technology assessment. As stated above, all adverse patient outcomes and medico-legal ramifications would be included in the comprehensive QA analysis conducted and stored in the database, to provide an objective means with which the institution/administrators can accurately gauge clinical efficacy.

The combined data obtained from subjective feedback and objective data collection and stored in the database 113, can in turn be used by the program 110 to create a comprehensive assessment of operational efficiency and performance as it relates to contrast administration.

In addition to clinical outcomes analysis, these data can also be used by the program 110 to perform an economic analysis of contrast administration in association with medical imaging examinations. By pooling data from multiple participating sites, a meta-analysis can be performed by the program 110 (taking into account institutional, technology, and patient-specific demographics) to provide "best clinical practice" guidelines and recommendations for improved economics, as it relates to contrast administration within medicine.

Best practice guidelines are typically created by a consensus panel of experts, based on available clinical data (which can be provided by pooling QA data). These expert panels are typically created by professional societies (e.g., American College of Radiology) and create guidelines for the heterogeneous group of end-users to follow. Because each clinical situation is unique (differences in institutional demographics, technology used, patient clinical status, etc.) the guidelines tend to be fairly general and appeal to the least common denominator, and will often make practice recommendations.

These clinical guidelines can be integrated by the program 110 into the various information and imaging technologies to serve as a reference. If and when guideline thresholds are exceeded (e.g., volume and specific type of contrast for a particular clinical indication), then an electronic warning can be provided by the program 110 to the end-user.

If, for example, the end-user decides to proceed in a manner different from the recommended guidelines, the program 110 can document the cause and justification (e.g., special research protocol) into the RIS 20 and/or PACS 30, or database 113. This provides the means with which end-users have full discretion to protocol the study in the manner they see fit, with data recorded by the program 110 for future analysis.

When external peer review is performed (in accordance with Joint Commission on Accreditation of Healthcare Organizations (JCAHO) requirements, for example), this technical data related to contrast administration provides a valuable adjunct in determining the role of contrast administration in overall assessment of imaging quality and diagnostic accuracy.

The Contrast Scorecard program 110 can also provide the end-user with educational links, which can take a number of forms including (but not limited to) peer review journals, FDA guidelines, basic science and clinical research (related to contrast), societal recommendations, and industry-related data relevant to imaging modalities, contrast agents, and contrast injectors. As an example, if a new contrast agent has just received FDA approval and is being marketed, a radiologist or clinician can enter the contrast agent of interest and receive, from the program 110, educational information and relevant clinical data from the Contrast/QA Scorecard databases 113. As data is collected within these Contrast and QA databases 113, alerts can be sent out to physicians by the program 10, with updates analyses, which assist them in their selection of specific diagnostic medical agents and protocol selection.

Administrators may also use individual, institutional, and national database records within the Contrast and QA Scorecard databases 113 to assist with the creation of operational standards, education and training, credentialing, and technology assessment.

As an example, if an administrator is considering the purchase of a new imaging modality, diagnostic medical agent, or contrast injector, he/she may consult the Contrast/QA database 113 to make an educated and data-driven decision.

If on the other hand, an administrator is being tasked with requests for new or expanded clinical privileges, they may consult the individual requestor's Contrast/QA Scorecard database 113 to obtain objective data which can be correlated with their peers to determine whether they meet accepted standards of practice. If the imaging department or any of its practitioners are deviating from accepted standards (relative to quality or safety), the administrator can utilize data contained within the Contrast and QA Scorecard databases 113 to assist with education and training.

Trending analysis is performed by the program 110 from this comprehensive QA database 113 with periodic reports (using a standardized template) issued by the program 110 to the various stakeholders assisting in the QA data collection (technologists, radiologists, clinicians, administrators). All adverse clinical outcomes initiate an immediate QA root cause analysis, and are stored in an additional "adverse outcomes" database 113. In addition, individual QA outliers (defined as beyond two standard deviations beyond local, regional, or national norms) are recorded by the program 110, which then initiates educational and peer review.

Third party payers may elect to promote participation in this QA analysis by offering financial incentives to those institutions, healthcare providers, and technology vendors that participate in data collection, standardization, and analysis.

Third party payers and credentialing agencies can also use the data contained within the Contrast and QA Scorecard databases 113 to make objective assessments of performance, as it relates to relevant peer groups. This is particularly relevant to Pay for Performance (P4P) programs, which are theoretically designed to offer economic incentives to those providers that exemplify high standards of clinical practice. The data contained within these Scorecards provides objective data related to quality and safety, while allowing for comparison within selected peer groups.

In the case of the Contrast Scorecard, imaging providers sharing pre-defined QA data with the public would be entitled to some financial incentive. In addition, those providers whose QA performance measures meet or exceed the threshold (e.g., rate of contrast extravasation) would also get a financial incentive. The financial incentive typically comes from a discretionary pool, such that a base compensation is allocated to all providers and the additional P4P fee added to that base.

Finally, this combined QA data could be made available by the program 110 over the Internet to assist in patient education and informed decision making.

Thus, the Diagnostic Medical Agent Scorecard provides representative lists of individual profiles which include the following: Radiologist, Clinician, Technologist, Aide, Department, Institution, Diagnostic Medical agent, Contrast injector (or other application device), and Modality.

In addition, the individual and institutional administration profiles include information on, for example, (Intravenous) Access, Screening (Safety Profile and EMR), Iatrogenic Complications, Utilization, and Technical Optimization Factors (Exam Protocols, Dose Optimization).

With respect to the Diagnostic Medical Agent (i.e., Contrast) Scorecard profiles, a number of variables are contained within each individual one specific to the individual entity being evaluated. The comprehensive list of variables tracked by the program 110 within the Contrast Scorecard may include, for example: patient safety, such as allergic reactions, side effects, organ toxicity, morbidity and mortality, contrast extravasation, intravenous access rates; contrast utilization, such as single exam volume, cumulative contrast dose, exam appropriateness, ionic vs. non-ionic contrast; contrast optimization, such as contrast efficiency (contrast time-activity quantitative analysis, multi-phasic contrast administration, and requirement for additional/repeat imaging; clinical utility and assessment, such as diagnostic accuracy, protocol optimization, level of diagnostic confidence; education and training, such as continuing education, database management, technical in-services; and technology assessment, such as bolus tracking, data collection and analysis, equipment quality control, and automated contrast cut-off; customer satisfaction; and economic analysis. The individual contrast profile represents a subset of variables from the comprehensive list, tailored to the specific responsibilities of each representative.

Specifically, the first category of patient safety metrics includes those adverse outcomes related directly to the contrast agent, including allergic reactions, non-allergic side effects, and organ toxicity. Allergic reactions to contrast are recorded by the program 110 in the database 113 according to both the frequency and severity of the allergic reaction, as well as any required intervention for treatment of the allergic reaction. Other non-allergic (idiosyncratic) side effects are also recorded by the program 110 which constitute adverse effects related to contrast administration, which are not the direct result of an allergic reaction (e.g., headaches, vomiting). Organ toxicity is recorded by the program 110 according to the specific organ damaged (e.g., kidney, liver) and the extent of toxicity (as recorded by organ-specific laboratory data tracked to organ function. This could include GFR and creatinine for the kidney and liver enzymes for the liver.

Also included in the patient safety category are iatrogenic complications related to the technical procedure of catheter insertion and contrast delivery. These variables include unsuccessful venous catheter insertion (frequency), contrast extravasation (frequency and volume), and tissue injury (e.g., AV fistula, pseudoaneurysm, hematoma, necrosis).

Further, the QA variables for the Diagnostic Medical Agent Scorecard that are included for the individual stakeholders include, for example: Technologist; Education and Training, Catheter Insertion, Iatrogenic Complications; Radiologist: Exam Appropriateness, Patient Safety Profile, Morbidity and Mortality; Clinician: Data Input, Exam Appropriateness, Clinical Assessment Feedback; Administrator: Staff Education and Training, Equipment Quality Control, Economic Analysis: Patient: Subjective Feedback (Satisfaction), Compliance; and Vendor: Data Collection, Injection Parameters.

Figure 2A:
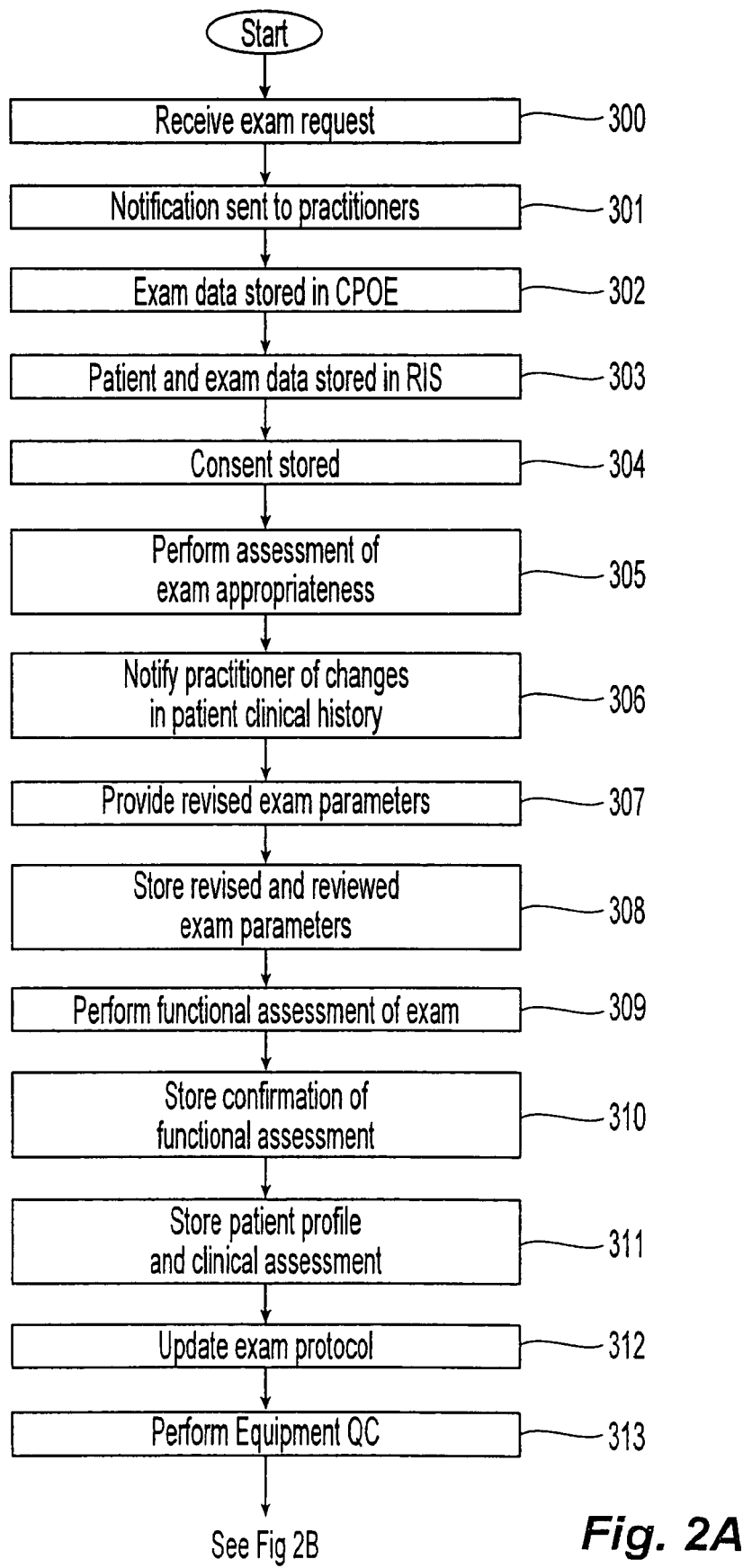
FIGS. 2A and 2B are flowcharts of steps taken to administer a diagnostic medical agent for an imaging examination according to one embodiment consistent with the present invention.
Figure 2B:
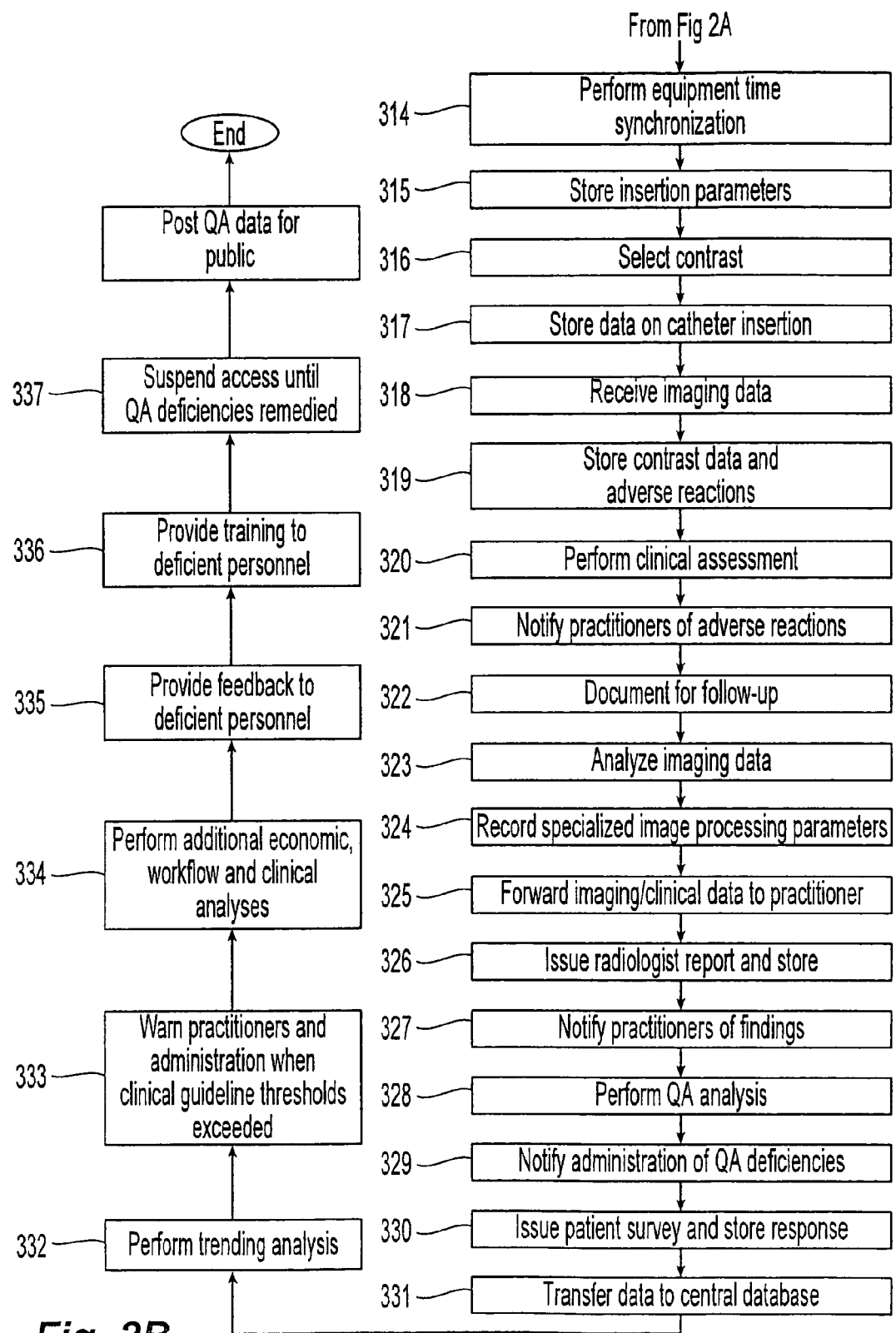

In operation (see FIGS. 2A and 2B), the program 110 receives a request for an examination by the referring clinician in step 300. Clinical, historical, and pertinent laboratory data are included with the request, and specific recommendations for the diagnostic medical agent (i.e., contrast) are also included in the requisition.

In step 301, the program 110 notifies the radiologist and technologist, for example, of the request for examination. If there are any questions, the technologist can arrange a direct consultation with the radiologist to clarify questions or concerns at the time of order entry.

Note that all users are subject to authentication and verification of access, training, and education, as well as their privileges being in good standing. If there is any problem with any of these parameters, then the program 110 may lock out the user, or prevent them from gaining access to certain programs etc., until the issue is removed or overcome.

All the relevant data are then integrated into the CPOE 15 (when available) in step 302.

When the patient arrives in the department of the institution at the time of the scheduled examination, the patient intake personnel verify the scheduled exam in step 303, and enter and store any pertinent patient and exam data into the RIS 20.

The patient is then escorted to the designated area for preparation, where the technologist obtains informed consent and enters same into the database in step 304, and answers any patient questions.

In step 305, an assessment of exam appropriateness may be performed by the program 110, where the program 110 will pull up previous exams and provide an indication of whether the exam would be suitable for this patient. If there has been a change in the patient's clinical history, the program 110 will perform an analysis in step 306, and notify the technologist.

In step 307, the program 110 will provide the technologist with any recommendations for the revised exam parameters, which are confirmed by the technologist, and stored by the program 110 in step 308.

In step 309, the program 110 performs a functional assessment of how the pre-selected imaging exam is to be performed.

In step 310, the functional assessment of the imaging exam is confirmed by the technologist or radiologist.

In step 311, the nurse and/or technologist (i.e., third party) performs the patient profile and clinical assessment, and the program 110 stores this information in the database 113.

The radiologist then reviews the exam protocol and makes any necessary modifications based on the available data, and the database 113 is updated in step 312.

The equipment QC is then performed by the technologist and the data stored in step 313 (although this step can be performed at any time prior to the patient's arrival).

In step 314, the program 110 performs a time synchronization between the injector 5 and the imaging equipment 21 to ensure that times recorded in both systems match to the nearest fraction of a second.

With the data stored in the database 113 on the parameters of the insertion in step 315, the program 110 makes the selection of the appropriate contrast in step 316. The technologist then approves the contrast selection and performs testing of the contrast.

In step 317, an intravenous catheter insertion is performed by an aide, nurse, or technologist, and any iatrogenic trauma associated therewith is recorded in the database 113.

In step 318, the examination (i.e., image acquisition) is then performed by the technologist.

The contrast injection data is collected (by the injector device), and recorded in the RIS 20, included any adverse data, and all stored by the program 110 in the database 113 in step 319.

The variables collected by the program 110 during the exam, including where the image fell in the contrast injection timing, including amount and pressure, and whether extravasation occurred, would allow the technologist to determine whether the contrast injection timing was adequate for the imaging and allow subsequent adjustment and fine tuning of the contrast injection on subsequent studies performed on the patient by updating and storing the parameters of the exam. This monitoring would also permit cumulative contrast amount tracking and also track the patient's GFR, creatinine, BUN, or other pertinent laboratory studies in the DICOM information, or in a separate file in the database 113.

After the exam, a clinical assessment of the patient and the IV site is performed by the nurse or technologist, and the data stored by the program in step 320.

In step 321, the radiologist and/or clinician is notified by the program 110 of any adverse reaction, and treatment is initiated. If no adverse reaction, the patient is given instructions prior to discharge.

In step 322, the program 110 documents for clinical or imaging follow-up, any issues associated with any information stored on catheter-related morbidity, and will electronically link the same with the primary imaging examination, in the computer database 113.

In step 323, the imaging data is reviewed and analyzed by the program 110 and by the radiologist, by primary interpretation of the initial imaging dataset, the analysis which is stored in the database 113 by the program 110. If additional data is required, the patient is recalled for additional imaging/contrast administration.

In step 324, the specialized image processing parameters used for image review and interpretation are recorded by the program 110 in the PACS 30 for future reference.

In step 325, pertinent imaging/clinical data is communicated by the program 110 to the referring clinician.

In step 326, the radiologist report is issued electronically and stored in the PACS 30 and EMR by the program 110. Any clinically relevant data (e.g., allergic reaction to contrast), is incorporated into the report by the program 110 and transferred to the patient EMR.

In step 327, the program 110 will notify the radiologist and clinician that direct consultation is required when there are unexpected/emergent findings, additional questions or clinical uncertainties, and adverse contrast reaction requiring treatment.

The program 110 will perform a QA analysis in step 328, and notify institutional or administrative personnel of any QA deficiencies in step 329.

In step 330, the program 110 issues a patient satisfaction survey to the patient, which is stored in the database 113 for comprehensive reporting. The administrative personnel, such as the QA team, will perform a review of the QA deficiencies and patient complaints.

In step 331, the program 110 transfers the individual data to a centralized QA database 113. The data is reviewed by a QA party to ensure that all non-related data is removed.

In step 332, the program 10 records the data and analyzes it for overall QA performance trends and identification of outliers. Thus, a comprehensive assessment of operational efficiency and performance as it relates to contrast administration is performed by the program 110. If clinical guideline thresholds are exceeded, an electronic warning can be provided by the program 110 to the end-user in step 333.

In step 334, the program 10 correlates the data with local, regional, and national standards, and performs additional analyses for economic, workflow, clinical outcomes.

In step 335, the program 110 performs a comparison analysis and determines whether there are deficient areas/individuals, and provides feedback and remedial education to those persons in step 336. However, the QA team will review the data to ensure that the record is accurately portrayed. In some cases, the program 110 will suspend access to the program 110, database 113, or logon privileges etc., until the QA team reviews the records or the deficient areas are corrected in step 337.

In step 338, the program 110 posts standardized QA data on the Internet for public dissemination.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. A computer-implemented method of selecting diagnostic medical agents for administration during an imaging examination on a patient, comprising:
    retrieving physiological diagnostic information on the patient from a database of a computer system;
    displaying said physiological diagnostic information on a display of a client computer of said computer system;
    receiving a request for an imaging examination at said client computer;
    performing an assessment of examination appropriateness for the patient by performing an analysis on the type of requested imaging examination in comparison with the physiological diagnostic information retrieved on the patient from said database;
    retrieving information on a plurality of diagnostic medical agents from said database of said computer system;
    performing a functional assessment of the imaging examination to be performed by determining parameters for administration of a diagnostic medical agent during conduct of the imaging examination in light of said physiological diagnostic information on the patient; and
    selecting and displaying on said display, an appropriate diagnostic medical agent for use during the imaging examination based on a result of an analysis of said examination appropriateness assessment and said functional assessment.

2. The method according to claim 1, further comprising:
    performing a QC analysis of imaging equipment used for the imaging examination.

3. The method according to claim 2, further comprising:
    performing a time synchronization between an injector which delivers the diagnostic medical agent and said imaging equipment to ensure that times on both are synchronous.

4. The method according to claim 3, acquiring technical data from said injector and storing said injector technical data in said database;
    wherein said injector technical data includes a type and volume of said diagnostic medical agent administered, injection rate and pressures, and contrast extravasation.

5. The method according to claim 4, wherein said injector technical data is directly correlated with said imaging equipment to provide a direct linkage between contrast delivery and derived imaging data.

6. The method according to claim 5, wherein images are obtained during different phases of diagnostic medical agent administration, to acquire and store said injector technical data.

7. The method according to claim 6, wherein said injector technical information is used to determine an optimal imaging/contrast protocol in accordance with said physiological diagnostic information on said patient.

8. The method according to claim 7, wherein imaging equipment acquisition parameters from prior imaging examinations, and corresponding image quality metrics stored in said database, are cross-referenced to identify optimum exposure parameters used in said imaging examination.

9. The method according to claim 1, further comprising:
    obtaining any iatrogenic trauma information associated with insertion of an intravenous catheter for delivery of said diagnostic medical agent to the patient; and
    receiving and storing said iatrogenic trauma information in said database.

10. The method according to claim 9, further comprising:
    obtaining QA data and diagnostic medical agent delivery data during the imaging examination,
    receiving and storing said QA data and diagnostic medical agent delivery data in said database.

11. The method according to claim 10, wherein said QA data and said diagnostic medical agent delivery data includes at least one of timing of an image acquisition during delivery of said diagnostic medical agent, and whether extravasation occurred.

12. The method according to claim 11, further comprising:
    performing a physiological diagnostic assessment of the patient after the imaging examination and after the catheter is removed; and
    receiving and storing said assessment in said database.

13. The method according to claim 12, further comprising:
    notifying a practitioner by electronic means, of any adverse reactions, unexpected or emergent findings, based on said clinical assessment.

14. The method according to claim 13, further comprising:

calendaring follow-up to the patient for additional information.

15. The method according to claim 14, further comprising;
performing an analysis of said physiological diagnostic data, image data, said QA data, and said diagnostic medical agent delivery data; and
providing a report of said analysis.

16. The method according to claim 15, further comprising:
including data on contrast extravasation, clinician orders, consultation notes, or follow-up procedures, in said report.

17. The method according to claim 13, wherein said adverse reactions or adverse outcomes are stored in a database and used for one of individual credentialing, institutional accreditation, provider education, pay for performance measures, or research and product development.

18. The method according to claim 12, further comprising:
obtaining any specialized image processing parameters assessed for the patient based on said functional assessment and on the imaging examination performed; and
receiving and storing said specialized image processing parameters in said database.

19. The method according to claim 18, further comprising:
notifying institutional personnel by electronic means, of any QA deficiencies in the examination or in performance of the personnel, based on said analysis.

20. The method according to claim 19, further comprising:
forwarding a patient survey to the patient, and storing a response to said patient survey in said database.

21. The method according to claim 20, further comprising:
performing a trending analysis of said analysis and said patient survey.

22. The method according to claim 21, further comprising:
obtaining best practice guidelines;
receiving and storing said best practice guidelines in said database;
performing a comparison of said QA data with said best practice guidelines; and
notifying institutional personnel by electronic means, when clinical guideline thresholds are exceeded based on said comparison.

23. The method according to claim 22, further comprising:
performing economic, workflow and clinical outcomes analyses of said QA data, clinical data, imaging data, and best practice guidelines comparison.

24. The method according to claim 23, further comprising:
posting standardized QA data from said analyses on the Internet for public dissemination.

25. The method according to claim 19, further comprising:
preventing computer access of any personnel found deficient in performance or training, until said deficiencies are overcome.

26. The method according to claim 1, further comprising:
incorporating information on the diagnostic medical agent into each individual image DICOM header.

27. The method according to claim 26, wherein said information includes a time and/or activity curve of each organ presented.

28. The method according to claim 27, wherein said time and/or activity curve is in a preselected color or size of font.

29. The method according to claim 26, wherein said information in said DICOM header includes one or more of: starting and ending times of said diagnostic medical agent administration, type of diagnostic medical agent, osmolality of diagnostic medical agent, total volume administered, delivery methodology, method of diagnostic medical agent administration, rate of diagnostic medical agent administration, anatomic site of access for delivery, catheter size, attenuation values, differential attenuation values, change in attenuation relative to pre-contrast rate of injection, complications, allergic reactions, treatment of complications, patient disposition, technology used, and data storage.

30. The method according to claim 1, wherein said functional assessment includes parameters on a presence or absence of said diagnostic medical agent, a manner in which said diagnostic medical agent is delivered, phases of image acquisition during said imaging examination, delivery of said diagnostic medical agent, and physiological diagnostic data, historical data and laboratory data unique to said patient.

31. The method according to claim 1, further comprising:
revising examination protocols based on said examination appropriateness assessment and said functional assessment.

32. The method according to claim 31, further comprising:
receiving confirmation of said revised examination protocols by said technologist.

33. The method according to claim 31, wherein said revision is performed by a radiologist.

34. The method according to claim 1, wherein change in patient physiological diagnostic status, indication for the imaging examination, and changes in technology used, are included in said functional assessment.

35. The method according to claim 34, wherein when said change in patient physiological diagnostic status is not available for said analysis of said examination appropriateness and said functional assessment, a user is provided with one of performing said imaging examination without administration of diagnostic medical agents, changing to an alternative imaging examination, or obtaining pertinent laboratory data prior to performing said imaging examination.

36. The method according to claim 1, further comprising:
receiving confirmation of said functional assessment by a technologist or radiologist.

37. The method according to claim 36, further comprising:
performing a patient profile and physiological diagnostic assessment of the patient after said functional assessment and prior to said imaging examination.

38. The method according to claim 36, wherein after selection of said appropriate diagnostic medical agent, said technologist approves same.

39. The method according to claim 1, further comprising:
tracking a bolus of diagnostic medical agent in the patient by a time/activity curve, which includes an injection rate of said diagnostic medical agent at a predetermined time period.

40. The method according to claim 39, further comprising:
obtaining a delayed set of images without injection of additional diagnostic medical agent; and
determining a period of time for said delayed set of images after injection of said bolus of diagnostic medical agent.

41. The method according to claim 39, wherein a slice of a patient image is shown on said time/activity curve on said display.

42. The method according to claim 1, further comprising:
providing a scorecard for said medical diagnostic agent used with said patient, said scorecard which includes at least one of: patient safety, including allergic reactions, side effects, organ toxicity, morbidity and mortality, contrast extravasation, or intravenous access rates; contrast utilization, including single exam volume, cumulative contrast dose, exam appropriateness, or ionic vs. non-ionic contrast; contrast optimization, including contrast efficiency; clinical utility and assessment, including diagnostic accuracy, protocol optimization, or level of diagnostic confidence; education and training, including continuing education, database management, or technical in-services; technology assessment, including bolus tracking, data collection and analysis, equipment quality control, or automated contrast cut-off; customer satisfaction; or economic analysis.

43. The method according to claim 1, further comprising: providing a list of quality assurance variables for said scorecard, including at least one of: education and training, catheter insertion, or iatrogenic complications for a technologist; exam appropriateness, patient safety profile, or morbidity and mortality for a radiologist; data input, exam appropriateness, or clinical assessment feedback for a clinician; staff education and training, or equipment quality control for an administrator; economic analysis for said patient including subjective feedback or compliance; and data collection or injection parameters for a vendor.

44. A computer system for selecting diagnostic medical agents for administration during an imaging examination on a patient, comprising:
at least one memory which contains at least one program which comprises the steps of:
retrieving physiological diagnostic information on the patient from a database;
displaying said physiological diagnostic information on a display of a client computer of said computer system;
receiving a request for an imaging examination at said client computer;
performing an assessment of examination appropriateness for the patient by performing an analysis on the type of requested imaging examination in comparison with the physiological diagnostic information retrieved on the patient;
retrieving information on a plurality of diagnostic medical agents from said database;
performing a functional assessment of the imaging examination to be performed by determining parameters for administration of an diagnostic medical agent during conduct of the imaging examination in light of said physiological diagnostic information on the patient; and
selecting and displaying an appropriate diagnostic medical agent for use during the imaging examination based on a result of an analysis of said examination appropriateness assessment and said functional assessment; and
a processor for executing the program.

45. A computer-readable medium containing executable code for selecting diagnostic medical agents for administration during an imaging examination on a patient, comprising:
retrieving physiological diagnostic information on the patient from a database, of a computer system;
displaying said physiological diagnostic information on a display of a client computer of said computer system;
receiving a request for an imaging examination at said client computer;
performing an assessment of examination appropriateness for the patient by performing an analysis on the type of requested imaging examination in comparison with the physiological diagnostic information retrieved on the patient from said database;
retrieving information on a plurality of diagnostic medical agents from said database of said computer system;
performing a functional assessment of the imaging examination to be performed by determining parameters for administration of an diagnostic medical agent during conduct of the imaging examination in light of said physiological diagnostic information on the patient; and
selecting and displaying, on said display, an appropriate diagnostic medical agent for use during the imaging examination based on a result of an analysis of said examination appropriateness assessment and said functional assessment.

46. A computer-implemented method of selecting diagnostic medical agents for administration during an imaging examination on a patient, comprising:
retrieving clinical information on the patient from a database of a computer system;
displaying said clinical information on a display of a client computer of said computer system;
receiving a request for an imaging examination at said client computer;
performing an assessment of examination appropriateness for the patient by performing an analysis on the type of requested imaging examination in comparison with the clinical information retrieved on the patient from said database;
retrieving information on a plurality of diagnostic medical agents from said database of said computer system;
performing a functional assessment of the imaging examination to be performed by determining parameters for administration of a diagnostic medical agent during conduct of the imaging examination in light of said clinical information on the patient;
selecting and displaying on said display, an appropriate diagnostic medical agent for use during the imaging examination based on a result of an analysis of said examination appropriateness assessment and said functional assessment;
receiving and storing in said database, any iatrogenic trauma associated with insertion of an intravenous catheter for delivery of said diagnostic medical agent to the patient;
receiving and storing images acquired, QA data received, and diagnostic medical agent delivery data received, during the imaging examination, in said database;
wherein said QA data and said diagnostic medical agent delivery data includes at least one of timing of an image acquisition during delivery of said diagnostic medical agent, and whether extravasation occurred;
receiving and storing a clinical assessment of the patient after the imaging examination and after the catheter is removed;
receiving and storing any specialized image processing parameters assessed for the patient based on said functional assessment and on the imaging examination performed; and
notifying institutional personnel by electronic means, of any QA deficiencies in the examination or in performance of the personnel, based on said analysis.

* * * * *